United States Patent [19]

Byrne et al.

[11] Patent Number: 5,852,047
[45] Date of Patent: Dec. 22, 1998

[54] PHARMACEUTICAL PRODUCT COMPRISING A SALICYLATE OF AN ESTERIFIABLE ACE-INHIBITOR

[75] Inventors: William Byrne, Dublin; Andrew Rynne, Clane, both of Ireland

[73] Assignee: Cal International Limited, Dublin, Ireland

[21] Appl. No.: 682,663

[22] PCT Filed: Jan. 27, 1995

[86] PCT No.: PCT/IE95/00012

§ 371 Date: Jul. 29, 1996

§ 102(e) Date: Jul. 29, 1996

[87] PCT Pub. No.: WO95/20571

PCT Pub. Date: Aug. 3, 1995

[30] Foreign Application Priority Data

Jan. 28, 1994 [IE] Ireland ..................... 940080

[51] Int. Cl.⁶ ............... A61K 31/40; C07D 207/08; C07D 207/12

[52] U.S. Cl. ............... 514/423; 514/428; 548/533
[58] Field of Search ............... 514/423, 428; 548/533

[56] References Cited

FOREIGN PATENT DOCUMENTS

| 55-15458 | 2/1980 | Japan . |
| 127556A | 4/1988 | Japan . |
| WO93/11136 | 6/1993 | WIPO . |

*Primary Examiner*—Johann Richter
*Assistant Examiner*—Jane C. Oswecki
*Attorney, Agent, or Firm*—Jacobson, Price, Holman & Stern, PLLC

[57] ABSTRACT

Salicylates of esterifiable ACE-inhibitors, especially captopril-S-aspirinate, and processes for their preparation are described. Such compounds are useful as analgesics, in the process of anti-clotting and as anti-hypertensive pharmaceutical reagents.

13 Claims, 9 Drawing Sheets

PHARMACEUTICAL PRODUCT COMPRISING A SALICYLATE OF AN ESTERIFIABLE ACE-INHIBITOR

This application is a 371 of PCT/IE95/00012 filed Jan. 24, 1995.

The invention relates to pharmaceutical products.

The term "ACE inhibitor" as used in this specification refers to pharmacologically active ACE inhibitor compounds which relieve, or act as prophylactic against cardiovascular disease including hypertension, cardiac failure, arrhythmias (irregular heart beats) and angina pectoris (pain in the heart muscle).

BACKGROUND OF THE INVENTION

ACE inhibitors act directly on the renin-angiotensin system. By inhibiting the angiotensin converting enzyme (ACE) they produce a decrease in blood pressure that can be sustained. ACE inhibitors also have a vasodilator effect which reduces peripheral resistance, increases natriuresis (the loss of sodium via the kidneys) and improves renal blood flow thereby assisting the antihypertensive (blood pressure lowering) effect.

The ACE inhibitors improve many of the haemodynamic parameters that are changed in congestive heart failure by inhibiting the formation of the vasoconstrictor, angiotensin II. They lower systemic arteriolar resistance through vasodilatation thus reducing the after load. Heart output and the cardiac index increase thereby increasing the stroke work and stroke volume. The resistance of the kidney vasculature is reduced which improves kidney blood flow leading to an increase in sodium loss via the kidneys thereby increasing body fluid loss which helps to reduce the blood volume returning to the heart. The removal of angiotensin II's stimulatory effect on aldosterone secretion also helps kidney sodium loss—for treatment in cardiac failure (heart failure).

Aspirin has been widely used for many years as an analgesic/anti-pyretic and anti-inflammatory agent. As such, it is a most useful drug. In more recent years, however, it has been discovered that aspirin has a powerful anti-platelet effect. Platelets are microscopic particles within the blood that, under certain circumstances, can stick together to form a thrombus (clot). Aspirin prevents the sticking together of platelets and thus helps prevent the occurrence of heart attack or its complications.

SUMMARY OF THE INVENTION

According to the invention there is provided a pharmaceutical product comprising a salicylate of an esterifiable ACE inhibitor.

The term "salicylate" as used in this specification refers to a salicylate or a salt, ester, derivative, complex thereof, or salts of the ester, derivative or complex having anti-platelet activity.

The term "esterifiable" as used in this specification means the formation of an ester, a thioester, an amide or an anhydride.

In a particularly preferred embodiment of the invention the product is formed by esterification of an esterifiable ACE inhibitor with acetylsalicylic acid.

Preferably the ACE inhibitor is captopril.

Alternatively the ACE inhibitor may be a primary amine such as Lisinopril. In this case the aspirinate may be formed by amide formation processes.

The ACE inhibitor may also be a secondary amine such as Enalapril, Enaliprilat, Perindopril, Perindoprilat, Quinapril or Ramipril. In this case, the aspirinate may be formed by amidation processes.

In another aspect the invention provides a process for preparing a pharmaceutical product of the invention which comprises esterifying an esterifiable ACE inhibitor such as a captopril with acetylsalicylic acid to form a thioester.

The invention further provides a process for preparing a pharmaceutical product of the invention which comprises forming an amide from an amine ACE inhibitor such as Lisinopril with acetylsalicylic acid.

The invention also provides a process for preparing a pharmaceutical product of the invention which comprises forming an anhydride from a secondary amine ACE inhibitor selected from Enalapril, Enaliprilat, Perindopril, Perindoprilat, Quinapril, and Ramipril with acetylsalicylic acid.

The invention also provides a process for preparing Captopril-S-aspirinate comprising the steps of:

protecting the phenol hydroxy group in salicylic acid;

activated coupling of the captopril thiol grouping with the activated salicylic acid;

removing protecting groups; and acetylation of the deprotected phenolic hydroxy to yield the desired captopril aspirinate.

In one embodiment of the invention, the phenol hydroxy group in salicylic acid is protected through benzyl ether formation. In a preferred embodiment, the salicylic acid is converted into O-benzyloxy benzoic acid.

Preferably, the protecting groups are removed by hydrogenolysis.

In one embodiment of the invention, the process includes the step of protecting the captopril carboxylic acid grouping.

In a preferred embodiment of the invention, the captopril carboxylic acid grouping is protected by methyl or benzyl ether formation.

In one embodiment, the activated coupling is carried out using pentafluorothiaphenol or 2,6 dichlorobenzyl anhydride in situ.

In another embodiment of the invention, the coupling comprises direct coupling of the activated salicylic acid with captopril using a direct coupling reagent. The direct coupling agent is preferably polyphosphate ester or phenyldichlorophosphate.

The invention also provides a pharmaceutical product whenever prepared by a process of the invention.

In another aspect, the invention provides a pharmaceutical composition including a pharmaceutical product of the invention. Preferably, the composition is in the form of a tablet or capsule.

DESCRIPTION OF PREFERRED EMBODIMENTS

The invention will be more clearly understood from the following description thereof given by way of example only.

ACE Inhibitors are N-Carboxyalkyl(peptide/lactam) derivatives. They include the following:

| Captopril | Acid | Hyd/Trest |
|---|---|---|
| Enalapril | Acid/Maleate | " |
| Enaliprilat | Acid/Base | " |
| Lisinopril | Acid/Base | " |
| Perindopril | Acid/Base | " |
| Perindoprilat | Acid/Base | " |
| Quinapril | Acid/Base | " |
| Ramipril | Acid/Base | " |

EXAMPLE 1

Synthesis of Captopril-S-aspirinate

Captopril is (S)-1-(3-mercapto-2-methyl-1-oxo-propyl)-L-proline [Merck Index 11th Edition No. 1773]
Materials:

| Acetylsalicylic acid | Sigma Limited | MW 180.16 |
|---|---|---|
| Captopril | | MW 217.28 |
| Dicyclohexylcarbodiimide (DCC) | Sigma Limited | MW 206.33 |
| Dimethylaminopyridine (DMAP) | Sigma Limited | MW 122.20 |

Figure 1:
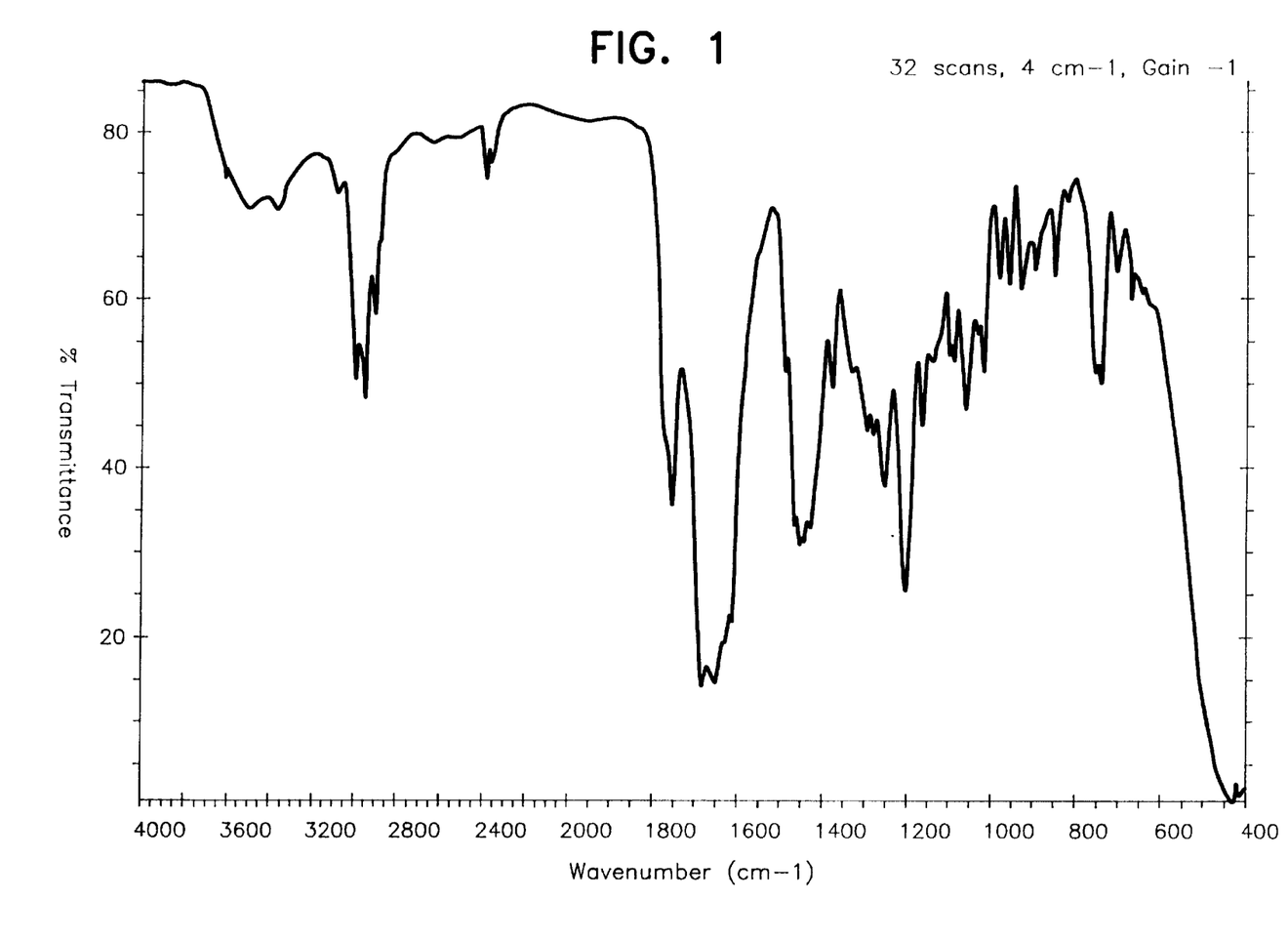
FIG. 1 is a FITR spectrum of a product obtained according to Example 1 of the present invention.
Figure 2:
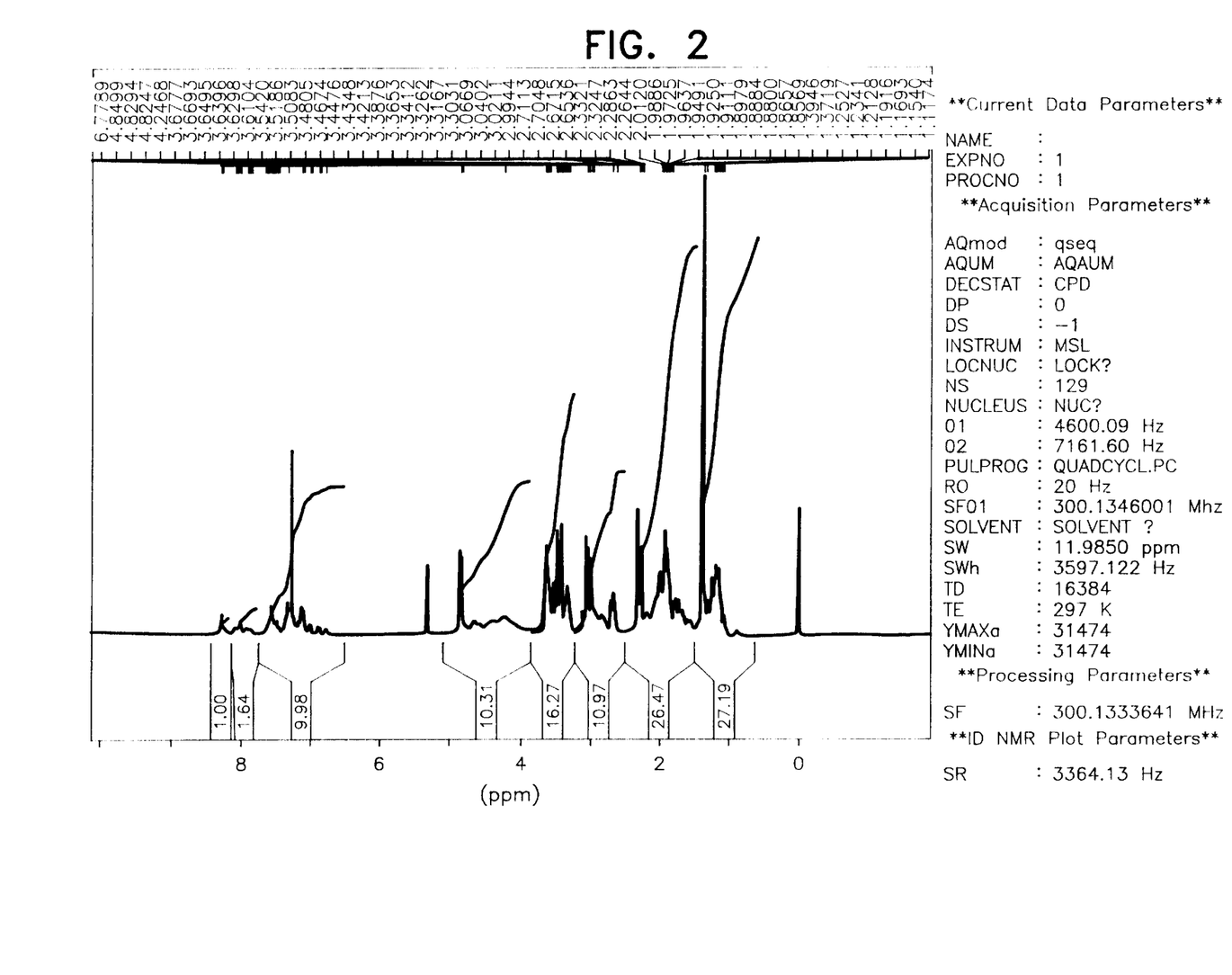
FIG. 2 is an NMR spectrum of a product obtained according to Example 1 of the present invention.

Method:
To a stirred solution of acetylsalicylic acid (2.7 gms, 0.15 mol) in 50 ml dry dichloromethane was added DMAP (0.3 gms) and captopril (3.3 gms, 0.15 mol). DCC (3.00 gms) was added gradually at 0° C. and the reaction mixture stirred for 15 minutes. The icebath was removed and the mixture stirred for a further 3 hours. The precipitated urea was removed by filtration and the filtrate evaporated in vacuo. The filtrate was taken up in dichloromethane and then washed with 2×25 ml portions of 20% citric acid and then by 2×25 ml portions of saturated sodium bicarbonate solution. The organic layer was dried over anhydrous sodium sulphate and the solvent removed in vacuo to yield the semisolid product captopril-S-aspirinate (Yield 25%). The product was characterised as captopril-S-aspirinate using FTIR and NMR as shown in appended spectra of FIGS. 1 and 2.
FTIR (thin film) vCO: 1754,1650 cm-1
NMR(CDCl$_3$,300 MHz).: 1.2δ,doublet CHCH$_3$: 2.4δsinglet ArOCOCH$_3$:1.6–2.8d aliphatic CH$_2$ and CH:4.62d doublet:7.28–8.2δ aromatics.

The product has the following structure:

Captopril-S-aspirinate

This method is illustrated schematically in Appendix 1 and is an adaptation of the method described by Neises and Steglich, Agnew Chem. Int. Ed. 17 (1978) No. 7, pages 522–524.

Other appropriate direct esterification methods are given in Larock, R. C., "Comprehensive Organic Transformations" pages 966–972 inclusive, published by VCH 1989.

EXAMPLE 2

2A Esterification via Acetylsalicyloyl Chloride (Appendix 2A)

Materials:

| Acetylsalicylic acid | Sigma |
|---|---|
| Thionyl chloride | Aldrich Chemicals |
| Captopril | |

Method:
In a 50 ml round bottomed flask equipped with a reflux condenser with drying tube attached, is placed 36 g acetylsalicylic acid. Thionyl chloride 35,2 gms is added gradually over 5 minutes. The mixture was heated under general reflux for 75 minutes and then cooled. The flask was then transferred to a rotatory evaporator in a fume hood and the excess thionyl chloride removed under vacuum. The required acetylsalicyloyl chloride was identified by infra red (v CO 1784cm–1) and nmr (acetyl methyl 3H:2.4δ and aromatics 4H:8.18 to 7.2δ).

Captopril (0.5 gms,3.75 mmol) was dissolved in 25 ml chloroform in a round bottomed flask appropriately protected from light and fitted with a drying tube. The acetylsalicyloyl chloride (~5.5 mls,37.5 mmol) was added gradually and the solution refluxed for 2 hours. The chloroform was evaporated in vacuo and the residue then taken up in ether. The ether was decolorised using charcoal, filtered, and the solvent removed in vacuo. The residue was then dissolved in ethanol and the product recovered by precipitation using n-hexane as an oily semisolid. The product (25% yield) was characterised as captopril-S-aspirinate using FTIR and NMR as per appended spectra.

This method is an adaptation of the method described by Anspach, R. et al, Ann. Chem. 367, 172–180, 1909. The product of example 1 may also be prepared by indirect esterification.

1) Satchell Q,Rev,Chem.Soc.,17.160–203 and 182–184, 1963, and

2) Scheithauer;Mayer Top.Sulfur Chem. 4,1–373,1979 may also be employed.

2B Masking of Carboxylic Acid Group in Captopril Followed by Esterification Using Acetylsalicyloyl Chloride (Appendix 2B)

Method:
Dissolve captopril (0.5 g) in methylene chloride (25 ml) and add 1.75 ml dihydropyran (Sigma Ltd) in 50 ml flask protected from light. Add TsOH (0.2 g) and stir at room temperature for 2 hours. Remove the solvent in vacuo and extract the residue with ether. The appropriate captopril THPester is recovered from a silica gel column after elution with methylene chloride. Yield ~80%.

Captopril-THP (0,5 g) ester is dissolved in dry methylene chloride in a round bottomed flask, fitted with a reflux condenser and a drying tube. Acetylsalicyloyl(~3 ml) is introduced gradually and then the mixture is refluxed for 1 hour. The solvent is removed in vacuo and the residue dissolved in ethanol. The aspirinate ester is precipitated using n-hexane.

The THP mask is removed by dissolving the ester in a mixture of THF(5 ml), Water—(2.5 ml) and then adding acetic acid (10 ml). The mixture is heated at 45° C. for 4 hours). After filtration the captopril-S-aspirinate was extracted from the reaction mixture using methylene chloride and recovered by elution from a silica gel column. The product was characterised using FITR and NMR as per appended spectra.

This method is based on the methods described in Bernardy, K. F. et al, J. Org. Chem. 44, 1438, 1979. Other suitable masking methods are described in the references cited in Chapter 5 pages 152–192 inc "Protective Groups in Organic Synthesis" by T W Greene, published by John Wiley & Sons, 1981.

2C Miscellaneous Methods Involving Dehydrating Agents

Esterification of thiols to form thioesters may also be achieved by treated carboxylic acids, eg. acetylsalicylic acids, with agents such as:

| | |
|---|---|
| Trisalkylthioboranes: | Pelter et al J. Chem. Soc., Perkin Trans. 1, 1672, 1977 |
| Phenyldichlorophosphate or the appropriate polyphosphate ester: | Immamoto et al Synthesis 134, 1982 Liu and Sabesan, Can J Chem 58, 2645, 1980 Dellaria et al Synth, Commun. 16, 1043, 1986 |
| Alkylchloroformate and triethylamine: | Kim and Kim, J. Org Chem 50, 560, 1985 |
| General: | Arrieta et al Synth. Commun. 13,471, 1983 Haslam Tetrahedron 36,2409–2433, 1980 |

EXAMPLE 3

Synthesis of Captopril-S-Aspirinate

We have found that the following method is preferred.

Strategy for the synthesis is outlined in the summary scheme below.

Summary of the overall reaction scheme

The starting material chosen for the synthesis was O-benzyloxy benzoic acid (4) which was synthesised by the pathway outlined in Scheme A.

Synthesis of O-Benzyloxy Benzoic acid (4).

-continued
Scheme A

1) Benzylation of Salicyclic acid

Salicyclic acid (1) was dissolved in methanol/water (10:1) and treated with potassium carbonate (1 eqv.) and then stirred at ambient temperature for one hour. The di-ionic salt (2) which was obtained by evaporation of the solvent mix was treated with two molar equivalents of benzyl bromide in dimethyl formamide (DMF) and heated to 60° C. for four hours. The solution was diluted with ether and extracted with water. The ether layer was dried with sodium sulphate, evaporated and chromatographed with petroleum spirit (b.p. 40°– 60° C.)—ether as eluent, on silica gel giving the dibenzyl salicylate (3).

2) Hydrolysis of Dibenzyl salicylate

Dibenzyl salicylate (3) was dissolved in a THF/methanol/water solution (2:1:1) and an equal volume of 2M sodium hydroxide was added. The solution was refluxed for fifteen minutes until the starting material had disappeared by TLC. The solution was poured into 100 ml of water and extracted with 3×30 ml of ether. The aqueous layer was acidified to pH3–4 with 2M hydrochloric acid. The acidic layer was similarly extracted with ether and the combined organic layers were dried over sodium sulphate and evaporated to yield the desired O-benzyloxy benzoic acid (4).

This O-benzyloxy acid can be used for the synthesis of the thioester using a number of different methods outlined below.

METHOD 1. Scheme B

O-Benzyloxy benzoic acid (4) and 1,4-dimethylamino pyridine (4 eqv.) were dissolved in dry toluene. The solution was heated to reflux and 2,6-dichlorobenzoylchloride (1 eqv.) was added. After ten minutes under reflux, Captopril in dry toluene was added and reflux was continued for a further thirty minutes. A second solution of 2,6-dichlorobenzoylchloride (1 eqv.) was added, followed by dry methanol (1 eqv.). Reflux was continued for a further thirty minutes. On cooling, filtration removed the inorganic salts and the filtrate was chromatographed using petroleum spirit (b.p. 40°–60° C.)—ethyl acetate gradient as eluent yielding the thioester (6) isolated as a white solid.

$^1$H and $^{13}$C NMR spectra, FIGS. 3 to 9, copies of which are attached, indicate the presence of both the aspirin and Captopril moieties in the product. This is seen clearly from the data below.

Figure 7:
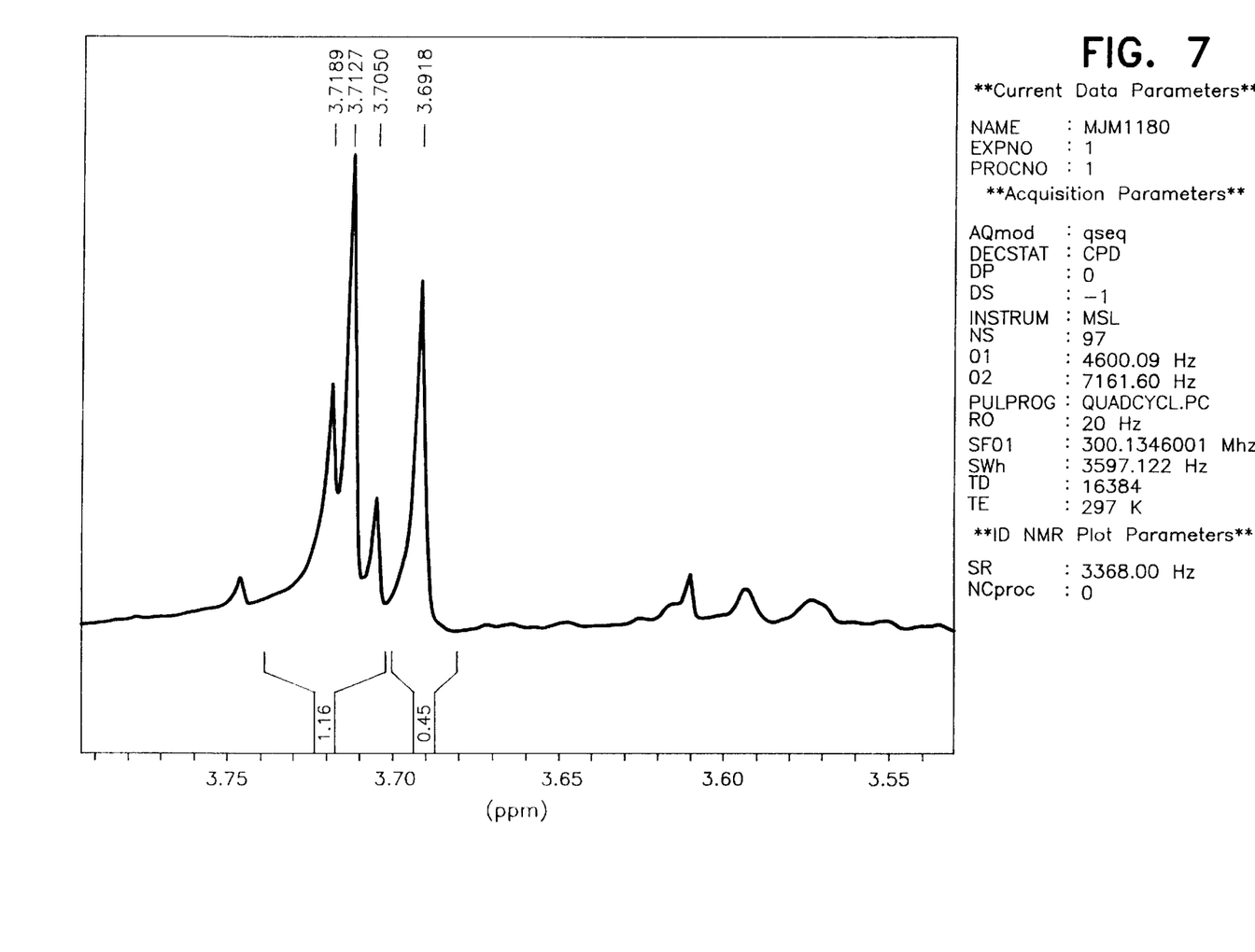
FIG. 7 is an $^1$H NMR spectrum of a product obtained according to Example 3, showing the presence of both Aspirin and Captopril moieties, between 3.55–3.9 ppm.

$^1$H NMR Spectrum:

(a) O-CH3, 3.69 ppm, singlet, FIG. 7.

Figure 6:
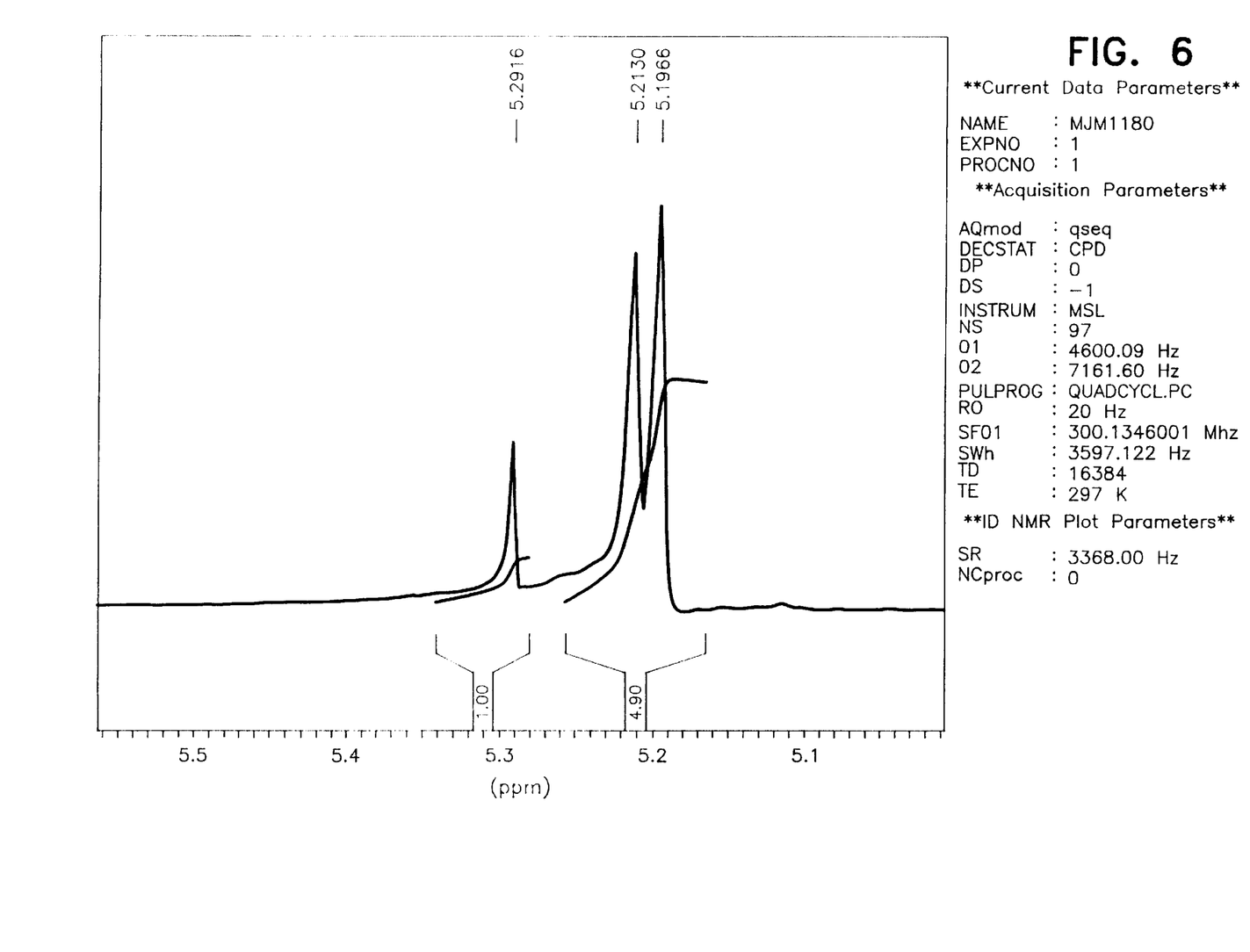
FIG. 6 is an $^1$H NMR spectrum of a product obtained according to Example 3, showing the presence of both Aspirin and Captopril moieties, between 4.9–5.5 ppm.

(b) O-CH2, 5.29 ppm, singlet, FIG. 6.

Figure 5:
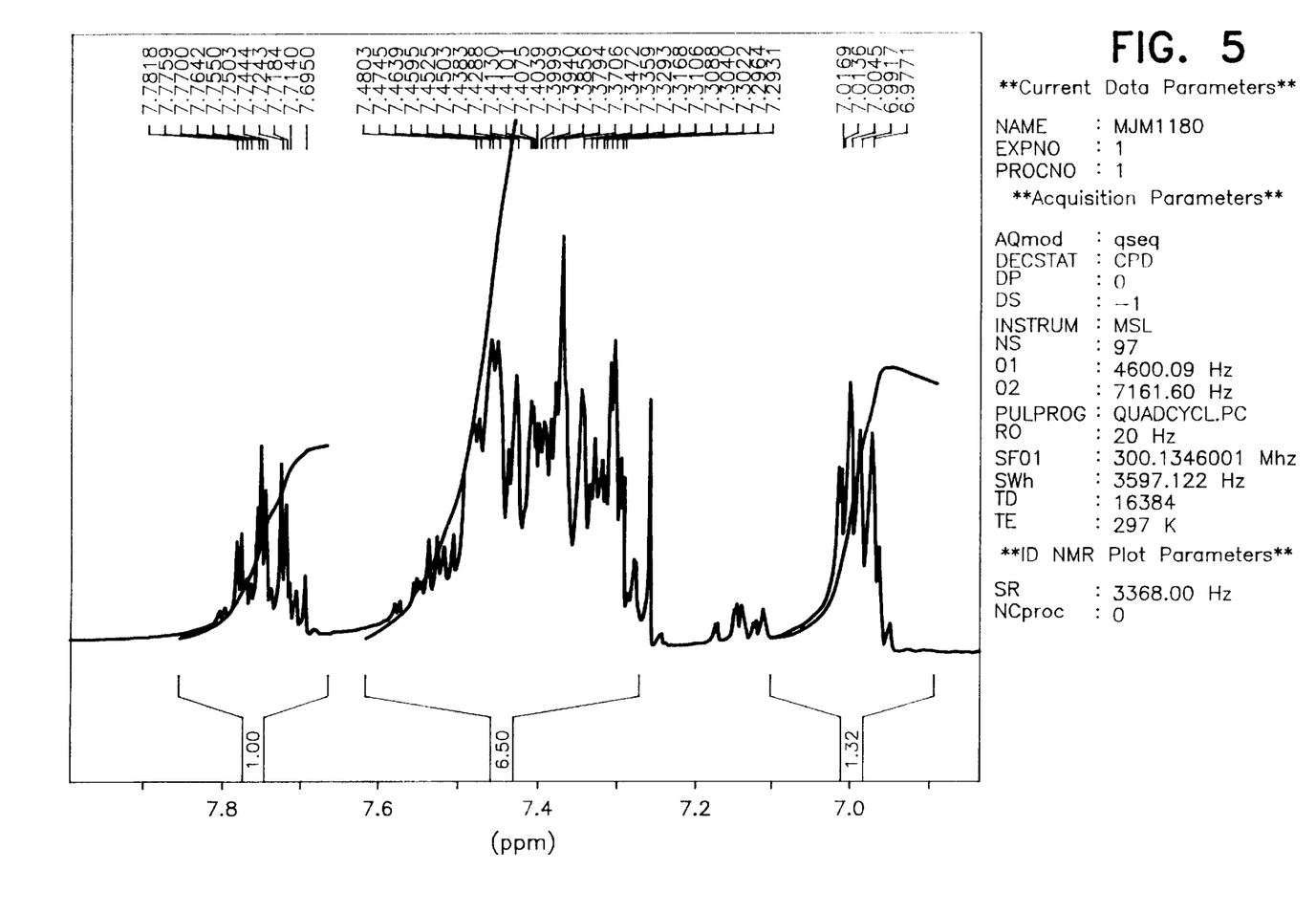
FIG. 5 is an $^1$H NMR spectrum of a product obtained according to Example 3, showing the presence of both Aspirin and Captopril moieties, between 6.8–8.0 ppm.

(c) aromatic benzyl protons, 6.97–7.01 ppm, multiplet, FIG. 5.

(d) aromatic aspirin & benzyl protons, 7.29–7.48 ppm, multiplet, FIG. 5.

(e) aromatic aspirin protons, 7.69–7.78 ppm, multiplet, FIG. 5.

$^{13}$C NMR Spectrum:

(a) CO-S, 191.48 ppm.

Figure 3:
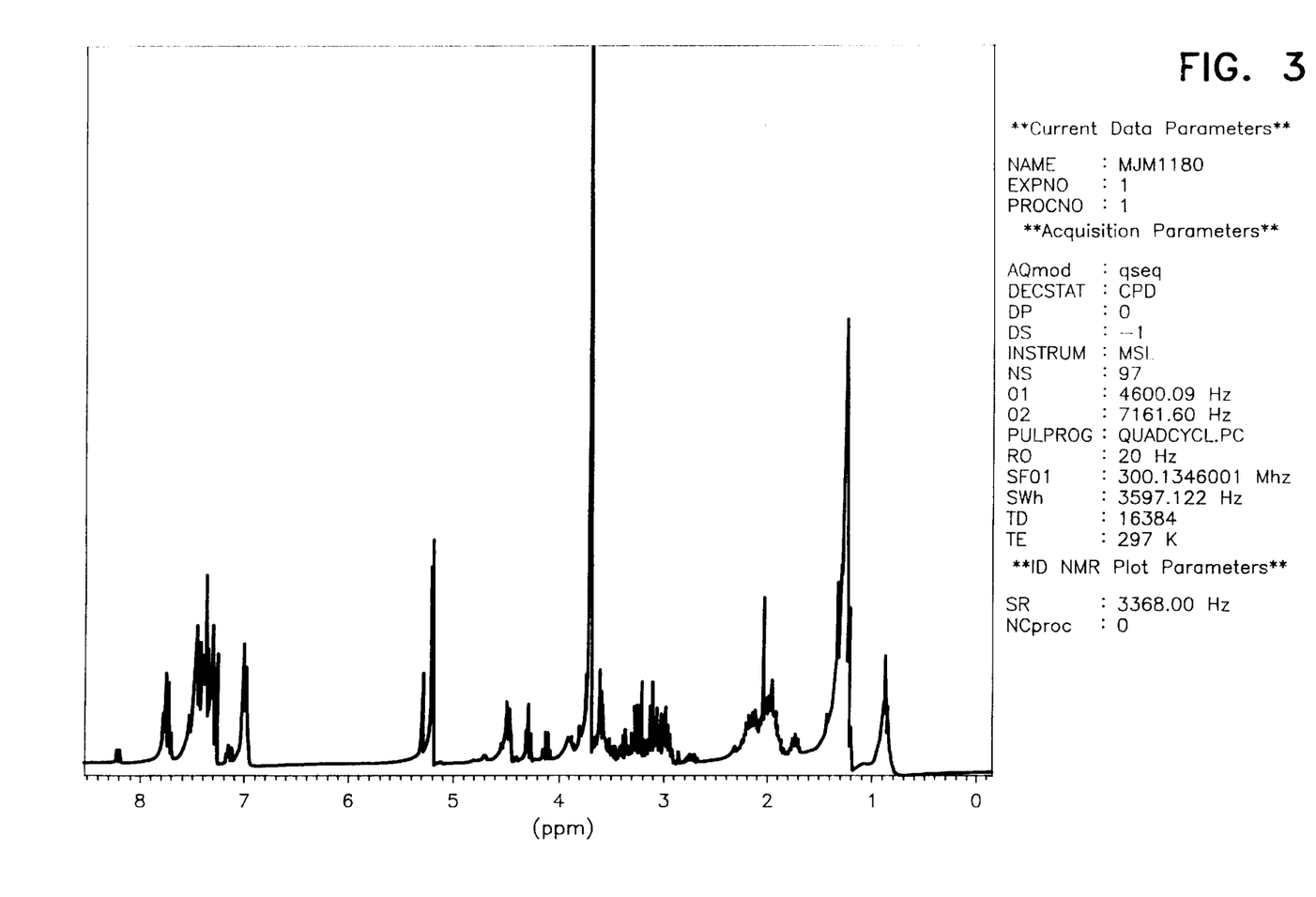
FIG. 3 is an $^1$H NMR spectrum of a product obtained according to Example 3, showing the presence of both Aspirin and Captopril moieties.

List of Spectra:

FIG. 3: $^1$H NMR 0–9 ppm.

Figure 4:
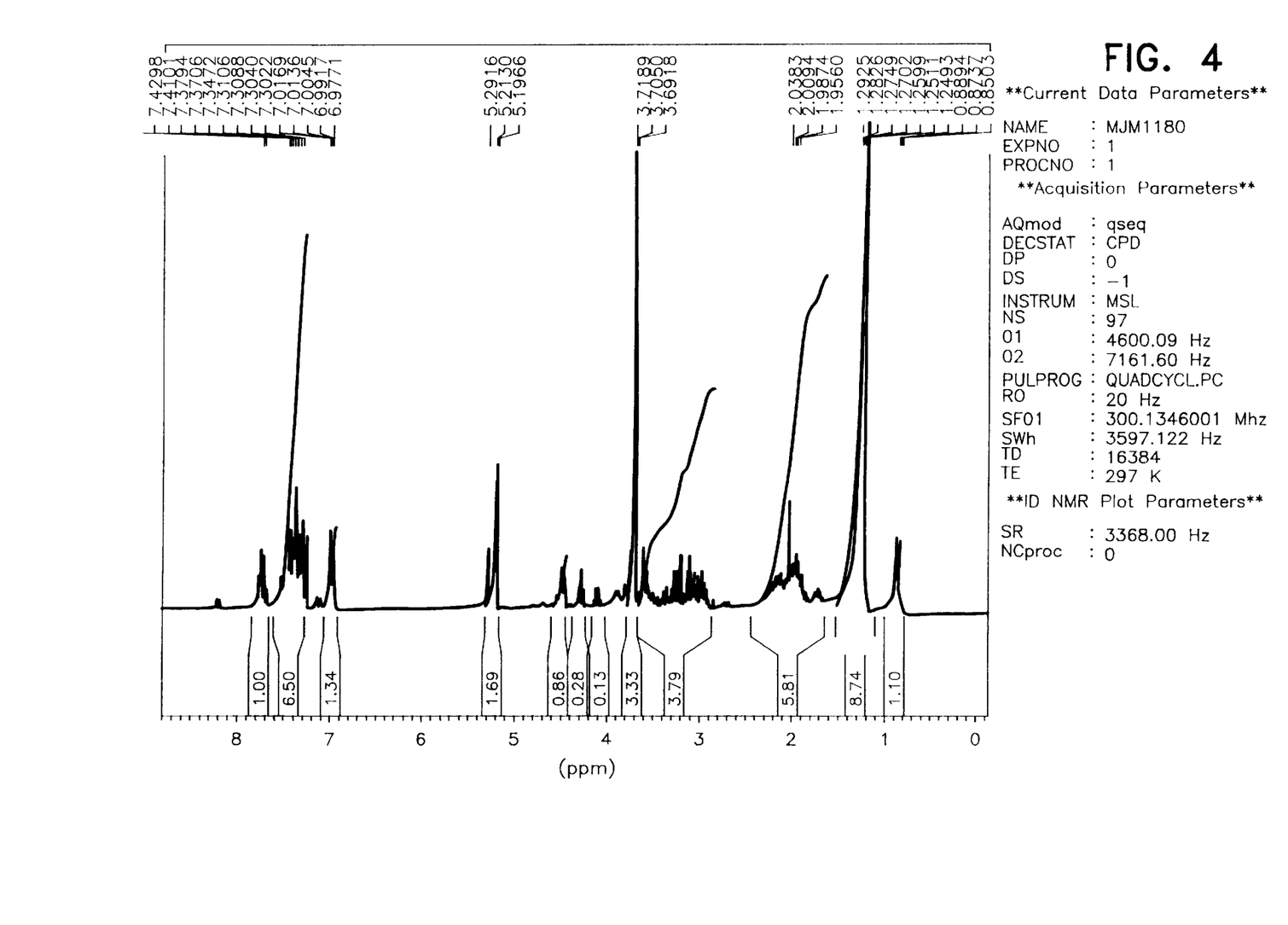
FIG. 4 is an $^1$H NMR spectrum of a product obtained according to Example 3, showing the presence of both Aspirin and Captopril moieties, the peaks being labeled and integrated.

FIG. 4: $^1$H NMR 0–9 ppm, peaks labelled & integrated.

FIG. 5: $^1$H NMR 6.8–8.0 ppm.

FIG. 6: $^1$H NMR 4.9–5.5 ppm.

FIG. 7: $^1$H NMR 3.55–3.9 ppm.

Figure 8:
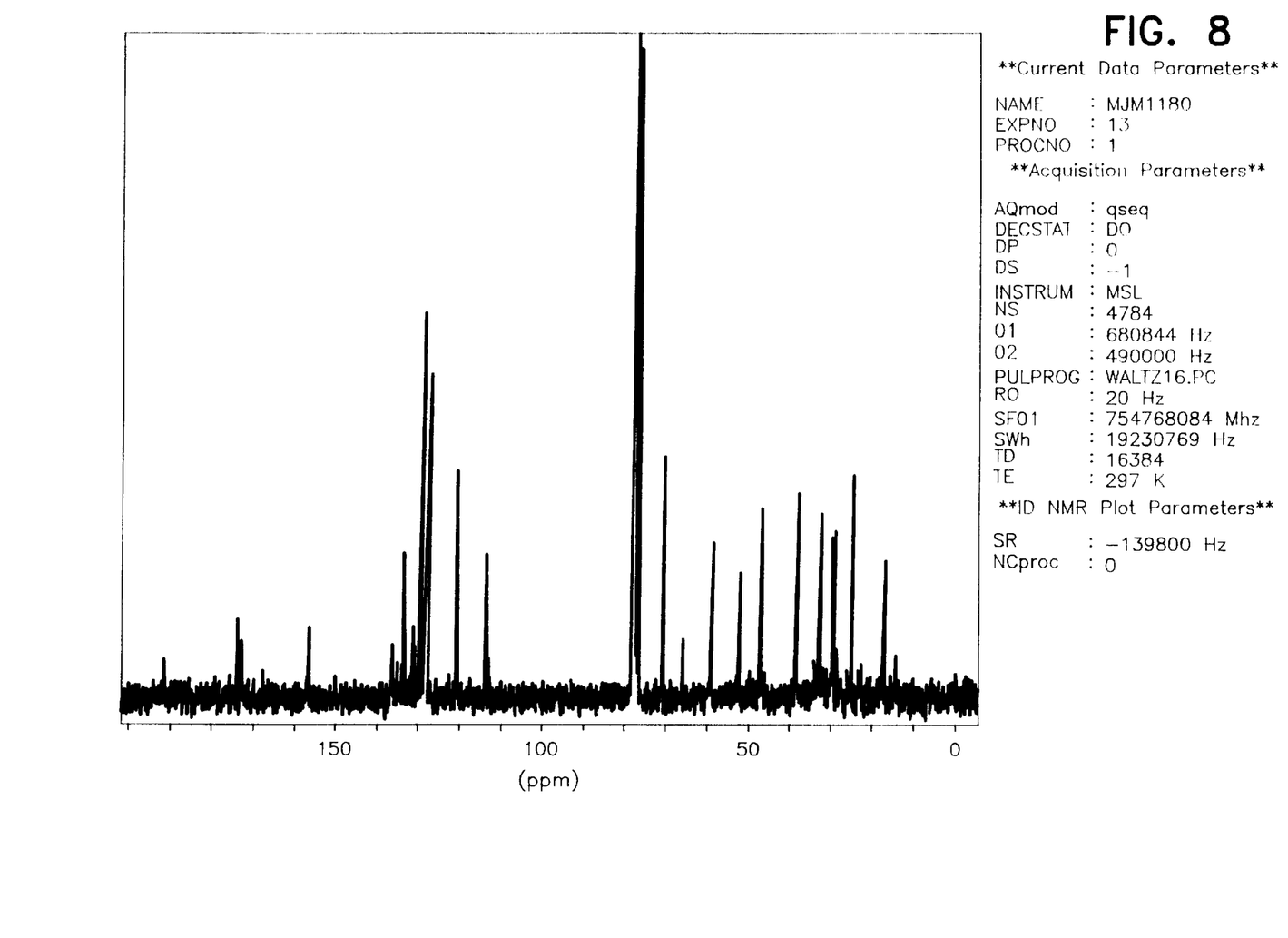
FIG. 8 is an $^{13}$C NMR spectrum of a product obtained according to Example 3, showing the presence of both Aspirin and Captopril moieties between 0–210 ppm.

FIG. 8: $^{13}$C NMR 0–210 ppm.

Figure 9:
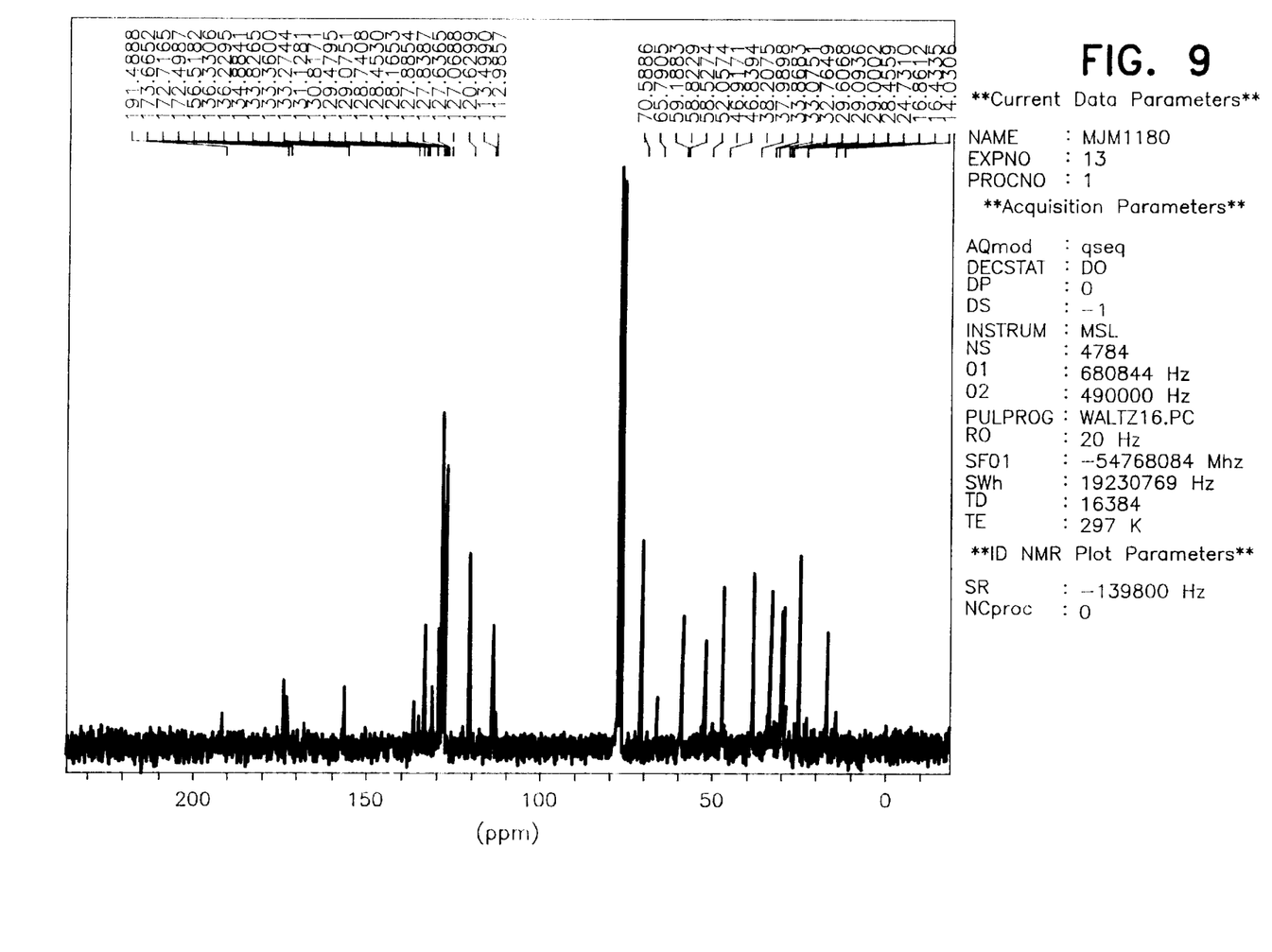
FIG. 9 is an $^{13}$C NMR spectrum of a product obtained according to Example 3, showing the presence of both Aspirin and Captopril moieties, between 0–210 ppm, wherein the peaks are labeled.

FIG. 9: $^{13}$C NMR 0–210 ppm peaks labelled.

Refs:

J. Inanaga, K. Hirata, H. Saeki, T. Katsuki & M. Yamaguchi, Bull, Chem. Soc. Jpn. 1979, 52, 1989.

P. P. Waanders, L. Thijs & B. Zwanenburg, Tetrahedron Lett. 1987, 28, 2409.

Method 2. Scheme C

-continued
Scheme C.

O-Benzyloxy benzoic acid (4) and 1,4-dimethylamino pyridine (4 eqv.) were dissolved in dry toluene. The solution was heated to reflux and 2,6-dichlorobenzoylchloride (1 eqv.) was added. After ten minutes under reflux, Captopril in dry toluene was added and reflux was continued for a further thirty minutes. A second solution of 2,6-dichlorobenzoylchloride (1 eqv. was added, followed by dry benzyl alcohol (1 eqv.). Reflux was continued for a further thirty minutes. On cooling, filtration removed the inorganic salts, the filtrate was chromatographed using petroleum spirit (b.p. 40°–60° C.)—ethyl acetate gradient as eluent yielding the thioester (7).

Method 3. Scheme D

O-Benzyloxy benzoic acid (4) and 1,4-dimethylamino pyridine (4 eqv.) were dissolved in dry toluene. The solution was heated to reflux and 2,6-dichlorobenzoylchloride (1 eqv.) was added. After ten minutes under reflux, Captopril in dry toluene was added and reflux was continued for a further thirty minutes. On cooling benzyl alcohol (1 eqv.) and DCC (1 eqv.) were added and the solution stirred at ambient temperature for three hours. Filtration removed the inorganic salts and the urea precipitate. The filtrate was chromatographed using petroleum spirit (b.p. 40°–60° C.)—ethyl acetate gradient as eluent yielding the thioester (7).
Ref:
B. Neises & W. Steglich, Angew. Chem. Int. Engl. 1978, 17, 522.

Method 4. Scheme E
Pentafluorobenzo-O-benzyloxy benzoate+Captopril+Anhydrous Cobalt chloride.

Scheme E

O-benzyloxy benzoic acid (4) was dissolved in dry DCM and treated with pentafluorophenol (1 eqv.) and DCC (1.1 eqv). The resulting solution was stirred at ambient temperature for five hours. Filtration removed the urea side product and column chromatography gave the desired ester (8).

Anhydrous cobalt (II) chloride (50–100 mg) was dissolved in dry acetonitrile and a mixture of the pentafluorobenzo-O-benzyloxy benzoate and Captopril (1 eqv.) in dry acetonitrile was added over five minutes. The resulting solution was stirred at ambient temperature, under nitrogen, in a darkened atmosphere for five hours. Acetonitrile was evaporated and the residue dissolved in diethyl ether. The ether layer was washed with a saturated solution of sodium bicarbonate followed by water. After drying and evaporation of the ether layer, the product (9) was isolated by column chromatography. Removal of the pentafluorophenol moiety was achieved by base hydrolysis using 2M sodium hydroxide in a THF/methanol/water solution. After ether extraction, the product (5) was purified by column chromatography.
Ref:
S. Ahmad & J. Iqbal, Tetrahedron Lett., 1986, 27, 3791.

Method 5. Scheme F

Alternatively different coupling reagents can be used for the direct thioester synthesis from the thiol and the benzyloxy acid:

(i) polyphosphate ester (PPE)[a]

(ii) phenyldichlorophosphate (PDP)[b]

a) T. Imamoto, M. Kodera & M. Yokoyama, Synthesis, 1982, 2, 135.
b) H. J. Liu & S. I. Sabesan, Can. J. Chem., 1980, 58, 2645.

Scheme F i) A mixture of O-benzyloxy benzoic acid (4) and Captopril (1.1 eqv.) and PPE (2–10 ml) was stirred at ambient temperature under nitrogen for fifteen hours. The reaction was treated with a saturated aqueous solution of sodium hydrogencarbonate (20 ml) and extracted with dichloromethane (DCM). The organic layer is dried over sodium sulphate and evaporated to dryness. The product (5) was isolated by column chromatography using petroleum spirit-ethyl acetate as eluent.

(ii) To a solution of the benzyloxy acid (4) in 1,2-dimethoxyethane at 0° C. were added pyridine (3 eqv.) and Captopril (1.5 eqv.) and PDP (1.1 eqv.). After stirring at ambient temperature for fifteen hours under nitrogen, the reaction was poured into ice-cold aqueous 1N sodium hydroxide and extracted with chloroform (or DCM). The extracts were washed with a saturated sodium sulphate solution (20 ml), water (20 ml) and dried over sodium sulphate. The residue on evaporation was chromatographed to give the thioester (5).

Other possible direct coupling reagents include:

Diphenylchlorophosphate

Diethylchlorophosphate

N,N-dimethylphosphoramidic dichloride

Diethylphosphorylcyanide

Diphenylphosphoryl azide

Carbonyl di-imidazole

2-Halopyridinium salts 2-halobenzothiazolium salts

DCC & N-Hydroxyphthalimide

REF:

E. Haslam, Tetrahedron Lett., 1980, 36 (17), 2409–2433.

In Methods 1–5 above, the thioester products obtained need to be debenzylated and in the case of product 6 demethylated. The free OH compound (10) is then acetylated. Scheme G.

Scheme G

5, R = H
6, R = ME
7, R = CH₂Ph

The thioester (5, 6 or 7) was dissolved in an ethanol/DCM (1:1) solution and treated with Pd-C (1 eqv. for product 5 and 2 eqv. for products 6 and 7). The mixture was stirred under an atmosphere of hydrogen and monitored by tl c until none of the starting material remained. The suspension was filtered through silica and the filtrate was evaporated to yield (10) which was dissolved in dry DCM. The solution was then treated with acetic anhydride (3 eqv.) followed by triethylamine (2 eqv.) and DMAP (4 eqv). The mixture was then stirred at ambient temperature for two hours. The solvent was evaporated and the residue was chromatographed, using petroleum spirit- ether as eluent, yielding the aspirinate thioester of Captopril (11).

The products of the invention are useful as in a single chemical entity a product which acts as an ACE inhibitor and also has anti-platelet activity as described above is provided.

The products may be formulated in any suitable pharmaceutical compositions using conventional excipients/vehicles. Usually, the pharmaceutical composition will be presented in a form for oral administration, preferably in a tablet or capsule form.

It will be appreciated that the composition may include a diuretic and potassium salts in a single tablet or capsule. The diuretic may be frusemide, amiloride, hydrochlorothiazide or a potassium sparing diuretic such as spironolactone or trimterene.

It will be appreciated that while the invention has been specifically described with reference to an aspirinate of captopril it may also be applied to other ACE inhibitors. In the case of a primary amine such as Lisinopril amide formation procedures which are similar in principle to the esterification procedures described above may be employed. In the case of a secondary amine such as Enalapril amidation procedures may be employed.

The invention is not limited to the embodiments hereinbefore described which may be varied in detail.

APPENDIX 1

Captopril-S-aspirinate

APPENDIX 2A

Esterification via acetylsalicyloyl chloride

Captopril-S-aspirinate

Appendix 2B

Masking method THP

-continued
Appendix 2B

Captopril-S-aspirinate

We claim:

1. Captopril-S-aspirinate.

2. A process for preparing Captopril-S-aspirinate comprising the steps of:

protecting the phenolhydroxy group in salicylic acid;

activated coupling of the captoprilthiol grouping with the activated salicylic acid;

removing protecting groups; and acetylation of the deprotected phenolic hydroxy to yield the desired captopril aspirinate.

3. The process as claimed in claim 2 wherein the phenol hydroxy group in salicylic acid is protected through benzyl ether formation.

4. The process as claimed in claim 2 wherein salicylic acid is converted into O-benzyloxy benzoic acid.

5. The process as claimed in claim 2 wherein the protecting groups are removed by hydrogenolysis.

6. The process of claim 2 further comprising protecting the captopril carboxylic acid grouping by methyl, benzyl or pentafluorophenol ester formation.

7. The process as claimed in claim 2 wherein the activated coupling is carried out using pentafluorophenol or 2,6 dichlorobenzoylchloride in situ.

8. The process as claimed in claim 2 wherein the coupling comprises direct coupling of the activated salicylic acid with captopril using a direct coupling reagent.

9. The process as claimed in claim 8 wherein the direct coupling reagent is selected from the group consisting of polyphosphate ester and phenyldichlorophosphate.

10. A pharmaceutical product comprising a salicylate of an esterifiable ACE-inhibitor, wherein said ACE-inhibitor is captopril.

11. A process for preparing a pharmaceutical product as claimed in claim 10 comprising esterifying captopril with acetylsalicylic acid to form a thioester.

12. A pharmaceutical composition comprising a pharmaceutical product as claimed in claim 10.

13. A pharmaceutical composition comprising captopril-S-aspirinate.

* * * * *